United States Patent [19]

Schneider et al.

[11] 4,322,423
[45] Mar. 30, 1982

[54] 4-PHENYL-4,5,6,7-TETRAHYDRO-THIENO(2,3-C)PYRIDINES AND SALTS THEREOF

[75] Inventors: Claus Schneider, Ingelheim am Rhein; Karl-Heinz Weber; Adolf Langbein, both of Gau-Algesheim; Wolf D. Bechtel, Appenheim; Karin Böke, Ingelheim am Rhein, all of Fed. Rep. of Germany

[73] Assignee: Boehringer Ingelheim GmbH, Ingelheim am Rhein, Fed. Rep. of Germany

[21] Appl. No.: 134,441

[22] Filed: Mar. 27, 1980

Related U.S. Application Data

[63] Continuation-in-part of Ser. No. 945,438, Sep. 25, 1978, abandoned.

[30] Foreign Application Priority Data

Oct. 15, 1977 [DE] Fed. Rep. of Germany ....... 2746443
Jul. 29, 1978 [DE] Fed. Rep. of Germany ....... 2833378

[51] Int. Cl.³ ................. C07D 495/04; C07D 495/14; A61K 31/44
[52] U.S. Cl. ..................................... 424/256; 546/80; 546/114
[58] Field of Search ................... 424/256; 546/114, 80

[56] References Cited

U.S. PATENT DOCUMENTS 3,651,068 3/1972 Suh ........................................ 546/80
4,104,390 8/1978 Ferrand et al. ..................... 546/114

FOREIGN PATENT DOCUMENTS 2812950 10/1978 Fed. Rep. of Germany ...... 546/114

Primary Examiner—Alan L. Rotman
Attorney, Agent, or Firm—Hammond & Littell, Weissenberger & Muserlian

[57] ABSTRACT

Compounds of the formula

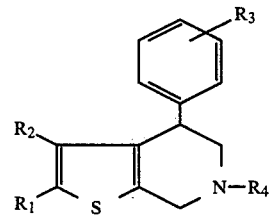

wherein $R_1$ is chlorine, bromine or alkyl of 1 to 3 carbon atoms;
$R_2$ is hydrogen or, when $R_1$ is alkyl, chlorine or bromine;
$R_1$ and $R_2$, together with each other, are straight alkylene of 3 to 4 carbon atoms;
$R_3$ is hydrogen, fluorine, chlorine, bromine, alkyl of 1 to 2 carbon atoms; hydroxyl or trifluoromethyl; and
$R_4$ is hydrogen, straight or branched alkyl of 1 to 4 carbon atoms or phenyl lower alkyl;

and non-toxic, pharmacologically acceptable acid addition salts thereof. The compounds as well as their salts are useful as antidepressants.

7 Claims, No Drawings

4-PHENYL-4,5,6,7-TETRAHYDRO-THIENO(2,3-C)PYRIDINES AND SALTS THEREOF

This is a continuation-in-part of copending application Ser. No. 945,438, filed Sept. 25, 1978, now abandoned.

This invention relates to novel 4-phenyl-4,5,6,7-tetrahydro-thieno[2,3-c]pyridines and non-toxic, pharmacologically acceptable acid addition salts thereof, as well as to a method of preparing these compounds, pharmaceutical compositions containing them as active ingredients, and methods of using them as antidepressants.

More particularly, the present invention relates to a novel class of 4,5,6,7-tetrahydro-thieno[2,3-c]pyridines represented by the formula

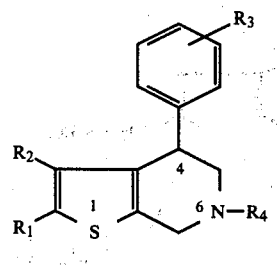

wherein
$R_1$ is chlorine, bromine or alkyl of 1 to 3 carbon atoms;
$R_2$ is hydrogen or, when $R_1$ is alkyl, chlorine or bromine; or
$R_1$ and $R_2$, together with each other, are straight alkylene of 3 to 4 carbon atoms;
$R_3$ is hydrogen, fluorine, chlorine, bromine, alkyl of 1 to 2 carbon atoms, hydroxyl or trifluoromethyl; and
$R_4$ is hydrogen, straight or branched alkyl of 1 to 4 carbon atoms or phenyl-lower alkyl, such as benzyl or phenethyl;
and non-toxic, pharmacologically acceptable acid addition salts thereof.

The compounds embraced by formula I above may be prepared by cyclizing a compound of the formula

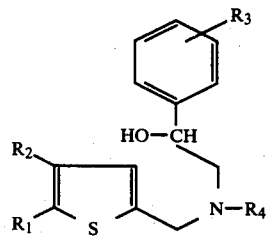

wherein $R_1$ through $R_4$ have the same meanings as in formula I. The cyclization may be carried out with an acid cyclizing agent, such as phosphoric acid, polyphosphoric acid, concentrated sulfuric acid or trifluoroacetic acid, in the absence of a solvent or in the presence of an inert solvent, such as methylene chloride, chloroform, dioxane, ethylene chloride, benzene, toluene, xylene, a chlorinated benzene or a mixture of any two or more of these, at a temperature between room temperature and the reflux temperature of the particular solvent or solvent mixture which is used.

However, the compounds of the formula I may also be prepared by first treating a compound of the formula II with a suitable chlorinating or esterifying agent, such as phosphorus trichloride, thionyl chloride or p-toluenesulfochloride, and subsequently cyclizing the reaction product with a suitable cyclizing agent such as phosphorus pentoxide or polyphosphoric acid, or also with a Friedel-Crafts catalyst such as aluminum chloride or tin chloride.

Those compounds of the formula I wherein $R_1$ is chlorine or bromine may also be obtained by conventional chlorination or bromination of a corresponding in 2-position unsubstituted 4,5,6,7-tetrahydro-thieno[2,3-c]pyridine. For bromination a compound of the formula I wherein $R_1$ is hydrogen, preferably in the form of of an acid addition salt, is reacted with elemental bromine in the cold or at room temperature in the presence of an organic acid such as acetic acid, or in the presence of an inert solvent, for instance, a chlorinated hydrocarbon such as carbon tetrachloride, methylene chloride or chloroform; the chlorination is advantageously effected with an excess of sulfuryl chloride, accompanied by mild heating.

Those compounds of the formula I wherein $R_1$ is alkyl of 1 to 3 carbon atoms and $R_2$ is hydrogen may also be chlorinated or brominated in the 3-position in the above-described manner. Compounds of the formula I wherein $R_4$ is hydrogen may be alkylated in the 6-position in conventional manner, for instance, by reaction with a dialkyl sulfate or an alkyl halide.

Using the above methods, the following compounds of the formula I may be obtained, for example:
2-chloro-4-phenyl-6-methyl-4,5,6,7-tetrahydro-thieno[2,3-c]pyridine,
2-chloro-4-(p-bromophenyl)-6-methyl-4,5,6,7-tetrahydro-thieno[2,3-c]pyridine,
2-chloro-4-(p-methylphenyl)-6-methyl-4,5,6,7-tetrahydro-thieno[2,3-c]pyridine,
2-chloro-4-(p-chlorophenyl)-6-methyl-4,5,6,7-tetrahydro-thieno[2,3-c]pyridine,
2-bromo-4-(p-methylphenyl)-6-methyl-4,5,6,7-tetrahydro-thieno[2,3-c]pyridine,
2-bromo-4-phenyl-6-methyl-4,5,6,7-tetrahydro-thieno[2,3-c]pyridine,
2-bromo-4-(p-bromophenyl)-6-ethyl-4,5,6,7-tetrahydro-thieno[2,3-c]pyridine,
2,6-dimethyl-4-phenyl-4,5,6,7-tetrahydro-thieno[2,3-c]pyridine,
2,6-dimethyl-4-(p-bromophenyl)-4,5,6,7-tetrahydro-thieno[2,3-c]pyridine,
2-bromo-4-(p-bromophenyl)-6-methyl-4,5,6,7-tetrahydro-thieno[2,3-c]pyridine,
2-chloro-4-(p-bromophenyl)-4,5,6,7-tetrahydro-thieno[2,3-c]pyridine,
2-chloro-4-(m-hydroxyphenyl)-4,5,6,7-tetrahydro-thieno[2,3-c]pyridine,
2,6-dimethyl-4-(p-chlorophenyl)-4,5,6,7-tetrahydro-thieno[2,3-c]pyridine,
2-methyl-4-(p-chlorophenyl)-6-isopropyl-4,5,6,7-tetrahydro-thieno[2,3-c]pyridine,
2,6-diethyl-4-(p-tolyl)-4,5,6,7-tetrahydro-thieno[2,3-c]pyridine,
2-methyl-4-(p-bromophenyl)-4,5,6,7-tetrahydro-thieno[2,3-c]pyridine,
2-methyl-4-(p-bromophenyl)-6-benzyl-4,5,6,7-tetrahydro-thieno[2,3-c]pyridine,
2-methyl-4-(p-bromophenyl)-6-phenylethyl-4,5,6,7-tetrahydro-thieno[2,3-c]pyridine,
2-propyl-4-(p-fluorophenyl)-6-methyl-4,5,6,7-tetrahydro-thieno[2,3-c]pyridine, 2,6-dimethyl-4-(m-trifluoromethylphenyl)-4,5,6,7-tetrahydro-thieno[2,3-c]pyridine, 2,6-dimethyl-3-chloro-4-(p-bromophenyl)-4,5,6,7-tetrahydro-thieno[2,3-c]pyridine, 2,6-dimethyl-3-bromo-4-(p-bromophenyl)-4,5,6,7-tetrahydro-thieno[2,3-c]pyridine, 4-(p-bromophenyl)-6-methyl-1,2,3,4,5,6,7,8-octahydro[1]benzo-thieno[2,3-c]pyridine, and 4-(p-bromophenyl)-6-n-propyl-1,2,3,4,5,6,7,8-octahydro[1]benzo-thieno[2,3-c]pyridine.

The starting compounds of the formula II may be obtained according to the following reaction scheme, either via the Schiff's base formed with a 2-phenyl-2-hydroxyethylamine or via 2-thienylmethylamine, which is reacted to form the starting compound II either with a bromoacetophenone or a styroloxide:

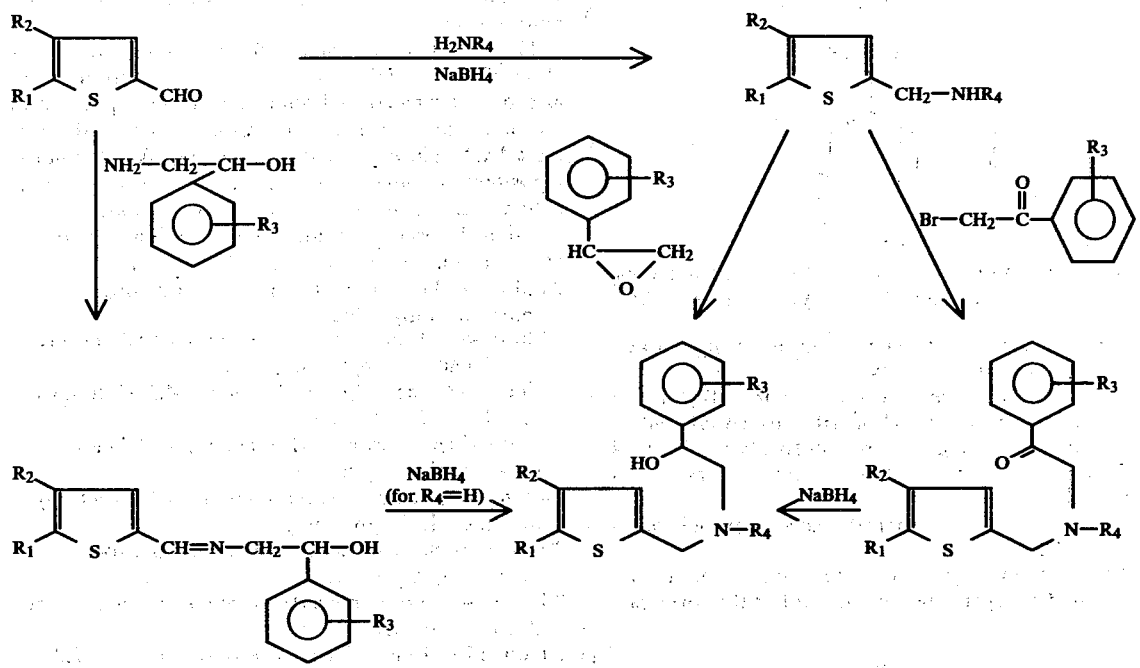

It is possible, but not absolutely essential, to isolate the starting compounds of the formula II thus prepared from the reaction mixtures; instead, the reaction mixtures containing them may be used directly for their cyclization into the desired end products of the formula I.

The compounds embraced by formula I are organic bases and therefore form acid addition salts with inorganic or organic acids. Examples of non-toxic, pharmacologically acceptable acid addition salts are those formed with a hydrohalic acid, sulfuric acid, phosphoric acid, aminosulfonic acid, formic acid, acetic acid, propionic acid, lactic acid, glycolic acid, gluconic acid, maleic acid, succinic acid, tartaric acid, benzoic acid, salicylic acid, citric acid, ascorbic acid, p-toluenesulfonic acid or oxyethane sulfonic acid.

The following examples illustrate the present invention and will enable others skilled in the art to understand it more completely. It should be understood, however, that the invention is not limited solely to the particular examples given below.

EXAMPLE 1

2,6-Dimethyl-4-(p-bromophenyl)-4,5,6,7-tetrahydro-thieno[2,3-c]pyridine

A solution of 50 gm (0.355 mol) of 2-methyl-5-(methylamino-methyl)-thiophene and 98.7 gm of p-bromo-ω-bromoaceto-phenone in 500 ml of ethanol was stirred with an equivalent quantity of potassium carbonate for 2 hours at room temperature. The resulting solution was then cooled to 5° C. 16.9 gm of sodium borohydride were then added in portions, and the mixture was stirred for 3 hours. For removal of the excess sodium borohydride, the mixture was poured over ice, extracted with methylene chloride and evaporated. The residue was chromatographed on silicagelmethylene chloride and yielded 96 gm (79.4% of theory) of N-methyl-N[2-methyl-thienyl-(5)-methyl]-2-(p-bromophenyl)-2-hydroxy-ethylamine, m.p. 145°–147° C.

30 gm (0.088 mol) of this ethylamine were stirred with 450 gm of polyphosphoric acid for 10 minutes at 30° C. The mixture was heated briefly to 90° C. and then slowly cooled. Subsequently, the mixture was decomposed with water, made alkaline with ammonia and extracted with ethyl acetate. This extract solution was slurried with activated charcoal and filtered through diatomaceous earth. After evaporation of the filtrate the residue, 2,6-dimethyl-4-(p-bromophenyl)-4,5,6,7-tetrahydro-thieno[2,3-c]pyridine, was dissolved in 800 ml of isopropanol; the hydrochloride precipitated upon addition of ethereal hydrochloric acid. 20.5 gm (65% of theory) of the hydrochloride of the formula

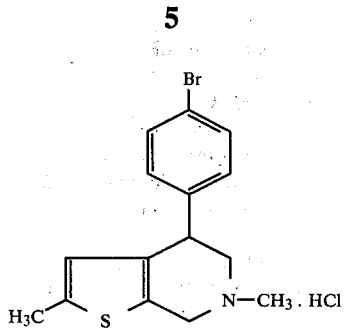

having a melting point of 258°–260° C. (recrystallized from isopropanol) were obtained.

EXAMPLE 2

2,6-Dimethyl-4-(p-bromophenyl)-4,5,6,7-tetrahydro-thieno[2,3-c]pyridine hydrochloride 3.45 gm (0.01 mole) of 2-methyl-4-(p-bromophenyl)-4,5,6,7-tetrahydro-thieno[2,3-c]pyridine hydrochloride, m.p. 282°–283° C., 50 ml of ether, 2.8 gm (0.02 mol) of potassium carbonate and 1.5 gm (0.01 mol) of methyl iodide were admixed, and the mixture was heated for 2 hours on a water bath. The inorganic salts were separated by suction filtration, the solvent was evaporated out of the filtrate, and the hydrochloride was precipitated from the residue with ethereal hydrochloric acid, and recrystallized from isopropanol. 3.25 gm (91% of theory) of 2,6-dimethyl-4-(p-bromophenyl)-4,5,6,7-tetrahydro-thieno[2,3-c]pyridine hydrochloride, m.p. 258°–260° C., were obtained.

EXAMPLE 3

2-Chloro-4-(m-hydroxyphenyl)-4,5,6,7-tetrahydro-thieno[2,3-c]pyridine 14.6 gm (0.1 mol) of 2-chloro-5-thiophenealdehyde, 18.9 gm (0.1 mol) of 1-(m-hydroxyphenyl)-2-amino ethanol hydrochloride and 14 gm of potassium carbonate were heated in 200 ml of benzene with 0.2 ml of trifluoroacetic acid at the boiling point for 4 hours in a vessel equipped with a water trap. The reaction mixture was then cooled to 5° C., and a solution of 4.2 gm of sodium borohydride in 100 ml of methanol was slowly added. The resulting mixture was stirred at 5° C. for 30 minutes. Most of the solvent was evaporated in vacuo and the residue was acidified with hydrochloric acid in order to decompose the excess sodium borohydride. Then, the mixture was neutralized with ammonia, extracted with ethylene chloride and evaporated, leaving as a residue 29.6 gm of an oil, which was dissolved in 150 ml of methylene chloride. The solution was cooled to 0° C., 120 ml of concentrated sulfuric acid were added dropwise, the mixture was stirred for 30 minutes at 0° C., subsequently poured over ice, neutralized with ammonia and extracted with ethyl acetate. After evaporation of the solvent, 8.4 gm (32% of theory) of the title compound, m.p. 188°–189° C. (from ethyl acetate), were obtained.

EXAMPLE 4

2,6-Dimethyl-3-bromo-4-(p-bromophenyl)-4,5,6,7-tetrahydro-thieno[2,3-c]pyridine hydrochloride 3 gm (0.008 mol) of 2,6-dimethyl-4-(p-bromophenyl)-4,5,6,7-tetrahydro-thieno[2,3-c]pyridine hydrochloride and 8 gm of aluminum bromide were dissolved in 100 ml of glacial acetic acid. The solution was cooled to 15° C., 1.4 gm of bromine were slowly added dropwise and the mixture was stirred several hours until the reaction had gone to completion. Then, the mixture was decomposed with ice water, made alkaline with ammonia, extracted with ethyl acetate and evaporated. The residue was chromatographed on silicagel with methylene chloride/methanol (95:5). Upon addition of ethereal hydrochloric acid, 2.25 gm (61% of theory) of the title compound, m.p. 261°–262° C., were obtained.

EXAMPLE 5

2-Chloro-4-phenyl-6-methyl-4,5,6,7-tetrahydro-thieno[2,3-c]pyridine hydrochloride A mixture consisting of 11 gm (0.068 mol) of 2-chloro-5-(methylamino-methyl)-thiophene, 50 ml of methanol and 8.2 gm (0.068 mol) of styroloxide was refluxed for 2 hours. The solvent was then evaporated in vacuo, and the residue was purified on silicagel with methylene chloride. 12.1 gm of an oil were obtained, which were heated in 100 ml of dioxane with 6.5 gm of phosphorus oxychloride and subsequently with 5.9 gm of phosphorus pentoxide. Excess phosphorus oxychloride and the solvent were removed in vacuo, the residue was admixed with water, made alkaline, extracted with methylene chloride, and purified on silicagel with methylene chloride. Upon treatment with ethereal hydrochloric acid, 17.9 gm (83% of theory) of the title compound, m.p. 223°–225° C. (from ethanol), were obtained.

Using procedures analogous to those described in the preceding examples, the following additional compounds of the formula I were prepared:

| Example No. | $R_1$ | $R_2$ | $R_3$ | $R_4$ | m.p. °C. HCl salt |
|---|---|---|---|---|---|
| 6 | Cl | H | p-Br | $CH_3$ | 257–259 |
| 7 | Br | H | p-$CH_3$ | $CH_3$ | 263–265 |
| 8 | Cl | H | p-$CH_3$ | $CH_3$ | 259–261 |
| 9 | Br | H | H | $CH_3$ | 210–212 (base) |
| 10 | $CH_3$ | H | H | $CH_3$ | 226–228 |
| 11 | Cl | H | p-Cl | $CH_3$ | 226–228 |
| 12 | Br | H | p-Br | $CH_3$ | 122–123 (base) |
| 13 | Br | H | p-Br | $C_2H_5$ | 258–259 |
| 14 | Cl | H | p-Br | H | 283–286 |
| 15 | $CH_3$ | H | p-Cl | $CH_3$ | 254–255 |
| 16 | $CH_3$ | H | p-Cl | i-$C_3H_7$ | 165–166 |
| 17 | $C_2H_5$ | H | p-$CH_3$ | $C_2H_5$ | 231–232 |
| 18 | $CH_3$ | H | p-Br | H | 282–283 |
| 19 | $CH_3$ | H | p-Br | —$CH_2$—$C_6H_5$ | 246–247 |
| 20 | $CH_3$ | H | p-Br | —$(CH_2)_2$—$C_6H_5$ | 144–146 |
| 21 | $C_3H_7$ | H | p-F | $CH_3$ | 228–230 |
| 22 | $CH_3$ | H | m-$CF_3$ | $CH_3$ | 246–248 |
| 23 | $CH_3$ | Cl | p-Br | $CH_3$ | 254–255 |

EXAMPLE 24

4-(p-Bromophenyl)-2-methyl-1,2,3,4,5,6,7,8-octahydro[1]benzothieno[2,3-c]pyridine hydrochloride (a) 4-(p-Bromophenyl)-1,2,3,4,5,6,7,8-octahydro[1]benzothieno[2,3-c]pyridine.

10 gm (0.04 mol) of N-(p-bromophenyl)-ethanolamine hydrochloride and an equivalent amount of potassium carbonate were added to a solution of 6 gm (0.036 mol) of tetrahydrobenzothiophene-2-aldehyde in 500 ml of methylene chloride, and the mixture was boiled for six hours in the presence of a catalytic amount of trifluoroacetic acid in a vessel equipped with a water trap. Thereafter, the precipitate which had formed was collected and dissolved in 100 ml of dimethylformamide, and the solution was reduced with 1.9 gm (0.05 mol) of sodium borohydride at room temperature. Subsequently, the reaction mixture was decomposed with water, extracted with ethyl acetate and evaporated, leaving 10 gm of the corresponding carbinol of the formula II. This intermediate product was, without further purification, slurried in methylene chloride and stirred at 0°–5° C. with 50 ml of sulfuric acid. The mixture was then poured over ice, made alkaline and extracted with methylene chloride. The extract solution was purified by chromatography on silicagel with ethyl acetate:methylene chloride:methanol (70:20:10) as the flow agent, yielding the desired base. Its hydrochloride, prepared from a solution of the base in acetone with hydrogen chloride, was obtained with a yield of 6.4 gm (74% of theory) and had a melting point of 214°–216° C.

(b) A solution of 2.5 gm (0.007 mol) of the end product of (a) in 50 ml of ethanol was admixed with 5 ml of formic acid and 5 ml of a 30% formalin solution, and the mixture was refluxed for twenty minutes, decomposed with ice water, made alkaline, extracted with ethyl acetate and evaporated. The residue was reprecipitated from ethereal hydrochloric acid, yielding 3 gm (75% of theory) of the hydrochloride of the formula

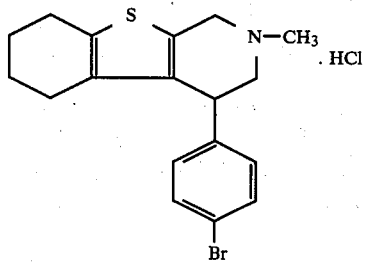

which had a melting point of 270°–272° C.

EXAMPLE 25

4-(p-Bromophenyl)-2-propyl-1,2,3,4,5,6,7,8-octahydro[1]benzothieno[2,3-c]pyridine A mixture of 0.3 gm (0.8 millimols) of the end product of Example 24(a), 10 ml of dimethylformamide, 1 ml of 1-bromo-propane and 1 gm of potassium carbonate was stirred for 12 hours at room temperature. Thereafter, the reaction mixture was admixed with water, extracted with methylene chloride, and the extracted solution was purified by chromatography on silicagel with cyclohexane:ethyl acetate (1:1) as the flow agent, yielding the title compound. Its hydrochloride, prepared with ethereal hydrochloric acid, was obtained with a yield of 0.2 gm (54% of theory) and had a melting point of 249°–250° C.

The compounds of the present invention, that is, those embraced by formula I above and their non-toxic, pharmacologically acceptable acid addition salts, have useful pharmacodynamic properties. More particularly, they exhibit antidepressant activity in warm-blooded animals, such as mice, which produces especially a thymoleptic, i.e. mood-elevating, and central stimulant effect.

It is known that various forms of depressions cause in certain sections of the brain a deficiency of biogenetic amines, especially of noradrenaline and serotonine; the biogenetic amines may be multiplied by inhibiting the uptake in the neurons. A suitable test arrangement has shown that the novel compounds inhibit above all the uptake of serotonine, but also that of noradrenaline, in the neurons. Therefore, they are clearly superior to known commercial products, for example, nomifensin, as the latter only inhibits the uptake of noradrenaline.

The test is performed on the homogenized, isolated cerebrum of the rat. A suspension of synaptosomes thus obtained is incubated with deuterated noradrenaline or serotonine and various concentrations of a solution of the test substance in water for ten minutes at 37° C. After completion of the incubation, the medium is separated by filtering, and the radioactivity of the suspension of synaptosomes is measured.

A control test without test substance is made simultaneously in order to determine the quantity of uptake of the radioactive amines.

The quantity of the test substance in mols which suffices for inhibiting 50% of the uptake is designated as IC 50.

A further test for determining the anti-depressant activity is the reserpine-antagonism, the elimination of the hypothermic effect caused by reserpine. The test is carried out on mice, using 5 animals per dose. 17 Hours after i.p. administration of 2 mg/kg of reserpine, the body temperature is measured peripherally at a room temperature of 19° C. Afterwards, the test substance is administered orally, and the body temperature is measured after elapse of 1, 3, 5, and 7 hours. For each measurement a medium effective dose ($ED_{50}$) is determined. This is the dose at which the body temperature of the animals treated with reserpine approaches the normal temperature of the untreated controls by 50%.

The following table shows the results:

| Compound | Reserpine antagonism mg/kg after | | | | Serotinine inhibition IC 50 (Mol) | Noradrenalin inhibition IC 50 (Mol) |
|---|---|---|---|---|---|---|
| | 1 hr. | 3 hrs. | 5 hrs. | 7 hrs. | | |
| 2-chloro-4-phenyl-6-methyl-4,5,6,7-tetrahydro-thieno[2,3-c] pyridine hydrochloride | 13 | 30 | 90 | 90 | $>10^{-5}$ | $1.4 \cdot 10^{-6}$ |
| 2-chloro-4-(4-bromophenyl)-6-methyl-4,5,6,7-tetrahydro-thieno [2,3-c] pyridine hydrochloride | 50 | 3 | 4.2 | 38 | $3.5 \cdot 10^{-6}$ | $1.0 \cdot 10^{-6}$ |
| 2-bromo-4-(p-tolyl)-6-methyl-4,5,6,7-tetrahydro thieno [2,3-c] pyridine hydrochloride | 48 | 80 | 80 | 80 | $9 \cdot 10^{-6}$ | $0.64 \cdot 10^{-6}$ |
| 2-chloro-4-(p-tolyl)-6-methyl-4,5,6,7-tetrahydro-thieno[2,3-c] pyridine hydrochloride | 44 | 12.5 | 18 | 20 | $>10^{-5}$ | $0.9 \cdot 10^{-6}$ |
| 2-chloro-4-(p-chlorophenyl)-6-methyl-4,5,67-tetrahydro-thieno [2,3-c] pyridine hydrochloride | 16 | 8.5 | 9.5 | 10 | $5.4 \cdot 10^{-6}$ | $1.6 \cdot 10^{-6}$ |
| 2,6-dimethyl-4-(p-bromophenyl-4,5,6,7- | 1.7 | 2.7 | 4.6 | 80 | $0.54 \cdot 10^{-6}$ | $0.28 \cdot 10^{-6}$ |

-continued

| Compound | Reserpine antagonism mg/kg after 1 hr. | 3 hrs. | 5 hrs. | 7 hrs. | Serotinine inhibition IC 50 (Mol) | Noradrenalin inhibition IC 50 (Mol) |
| --- | --- | --- | --- | --- | --- | --- |
| tetrahydro-thieno[2,3-c] pyridine hydrochloride | | | | | | |
| 2-bromo-4-(p-bromophenyl)-6-methyl-4,5,6,7-tetrahydro-thieno[2,3-c]pyridine | 55 | 7.5 | 32 | 100 | $4.1 \cdot 10^{-6}$ | $1.6 \cdot 10^{-6}$ |
| 2,6-dimethyl-4-phenyl-4,5,6,7-tetrahydro-thieno[2,3-c]pyridine hydrochloride | 19 | 25 | 80 | 80 | $8 \cdot 10^{-5}$ | $0.56 \cdot 10^{-6}$ |
| 2-bromo-4-phenyl-6-methyl-4,5,6,7-tetrahydro-thieno[2,3-c]pyridine | — | — | — | — | $5.4 \cdot 10^{-5}$ | $2.3 \cdot 10^{-6}$ |

For pharmaceutical purposes the compounds of the present invention are administered to warm-blooded animals perorally, parenterally or rectally as active ingredients in customary dosage unit composition, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0166 to 1.25 mgm/kg body weight, preferably from 0.083 to 0.83 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLES 26

Coated Pills

The pill core composition is compounded from the following ingredients:

| | |
| --- | --- |
| 2-Methyl-4-(p-bromo-phenyl)-6-methyl-4,5,6,7-tetrahydro-thieno[2,3-c]pyridine hydrochloride | 25.0 parts |
| Lactose | 50.0 parts |
| Corn starch | 22.0 parts |
| Gelatin | 2.0 parts |
| Magnesium stearate | 1.0 parts |
| Total | 100.0 parts |

Preparation

The active ingredient is intimately admixed with the lactose and the corn starch, the mixture is moistened with an aqueous 10% solution of the gelatin, the moist mass is granulated by passing it through a 1 mm-mesh screen, and the granulate is dried at 40° C. and again passed through the screen. The granulate is admixed with the magnesium stearate, and the mixture is compressed into 100 mgm-pill cores which are then coated with a thin shell consisting essentially of a mixture of sugar, titanium dioxide, talcum and gum arabic. Each coated pill is an oral dosage unit composition containing 25 mgm of the active ingredient.

EXAMPLE 27

Tablets

The tablet composition is compounded from the following ingredients:

| | |
| --- | --- |
| 2-Chloro-4-(p-chloro-phenyl)-6-methyl-4,5,6,7-tetrahydro-thieno[2,3-c]pyridine hydrochloride | 10.0 parts |
| Lactose | 40.0 parts |
| Corn starch | 44.0 parts |
| Soluble starch | 5.0 parts |
| Magnesium stearate | 1.0 parts |
| Total | 100.0 parts |

Preparation

The active ingredient and the magnesium stearate are intimately admixed with each other, the mixture is moistened with an aqueous solution of the soluble starch, the moist mass is granulated through a screen, and the granulate is dried and throroughly admixed with the lactose and the corn starch. The resulting composition is compressed into 100 mgm tablets. Each tablet is an oral dosage unit composition containing 10 mgm of the active ingredient.

EXAMPLE 28

Suppositories

The suppository composition is compounded from the following ingredients:

| | |
| --- | --- |
| 2-Chloro-4-(p-bromo-phenyl)-6-methyl-4,5,6,7-tetrahydro-thieno [2,3-c] pyridine hydrochloride | 10.0 parts |
| Suppository base (e.g. cocoa butter) | 1,690.0 parts |
| Total | 1,700.0 parts |

Preparation

The active ingredient, finely pulverized, is homogeneously stirred into the molten suppository base at 40° C. with an immersion homogenizer. The mixture is then cooled to 35° C. and 1700 mgm portions thereof are poured into cooled suppository molds and allowed to harden therein. Each suppository is a rectal dosage unit composition containing 10 mgm of the active ingredient.

EXAMPLE 29

Hypodermic solution

The solution is compounded from the following ingredients:

| | |
| --- | --- |
| 2-Methyl-4-(p-bromo-phenyl)-4,5,6,7-tetrahydro-thieno [2,3-c] pyridine hydrochloride | 5.0 parts |

| -continued | |
|---|---|
| Sodium pyrosulfite | 1.0 parts |
| Disodium salt of EDTA | 0.5 parts |
| Sodium chloride | 8.5 parts |
| Double-distilled water q.s.ad | 1000.0 parts |

Preparation

The active ingredient and the excipients are dissolved in a sufficient amount of double-distilled water, and the solution is diluted with additional double-distilled water to the desired concentration and then filtered until free from suspended particles. The filtrate is filled under aseptic conditions into 1 cc-ampules which are subsequently sterilized and sealed. Each ampule contains 5 mgm of the active ingredient.

Any of the other compounds embraced by formula I or a non-toxic, pharmacologically acceptable acid salt thereof may be substituted for the particular active ingredient in Examples 26 through 29. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

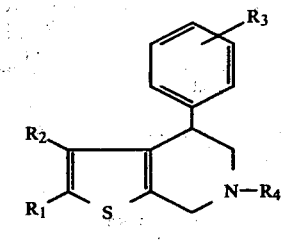

wherein
$R_1$ is chlorine, bromine or alkyl of 1 to 3 carbon atoms;
$R_2$ is hydrogen or, when $R_1$ is alkyl, chlorine or bromine; or
$R_1$ and $R_2$, together with each other, are straight alkylene of 3 to 4 carbon atoms;
$R_3$ is hydrogen, fluorine, chlorine, bromine, alkyl of 1 to 2 carbon atoms, hydroxyl or trifluoromethyl; and
$R_4$ is hydrogen, straight or branched alkyl of 1 to 4 carbon atoms or phenyl-lower alkyl;
or a non-toxic, pharmacologically acceptable acid addition salt thereof.

2. A compound of claim 1, which is 2-methyl-4-(p-bromo-phenyl)-6-methyl-4,5,6,7-tetrahydro-thieno[2,3-c]pyridine or a non-toxic, pharmacologically acceptable acid addition salt thereof.

3. A compound of claim 1, which is 2-chloro-4-(p-chloro-phenyl)-6-methyl-4,5,6,7-tetrahydro-thieno[2,3-c]pyridine or a non-toxic, pharmacologically acceptable acid addition salt thereof.

4. A compound of claim 1, which is 2-chloro-4-(p-bromo-phenyl)-6-methyl-4,5,6,7-tetrahydro-thieno[2,3-c]pyridine or a non-toxic, pharmacologically acceptable acid addition salt thereof.

5. A compound of claim 1, which is 2-methyl-4-(p-bromo-phenyl)-4,5,6,7-tetrahydro-thieno[2,3-c]pyridine or a non-toxic, pharmacologically acceptable acid addition salt thereof.

6. An antidepressant pharmaceutical dosage unit composition consisting essentially of an inert pharmaceutical carrier and an effective antidepressant amount of a compound of claim 1.

7. The method of elevating the mood of a warm-blooded animal in need thereof, which comprises perorally, parenterally or rectally administering to said animal an effective mood-elevating amount of a compound of claim 1.

* * * * *